(12) United States Patent
Stana et al.

(10) Patent No.: US 7,880,885 B1
(45) Date of Patent: Feb. 1, 2011

(54) PORTABLE EVALUATION OF WINDOW TRANSMISSION

(75) Inventors: James M. Stana, Orlando, FL (US);
Ronald H. Gilmore, Sanford, FL (US);
Kevin F. Williams, Orlando, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 267 days.

(21) Appl. No.: 12/270,611

(22) Filed: Nov. 13, 2008

(51) Int. Cl.
*G01N 21/00* (2006.01)
*G01N 21/55* (2006.01)

(52) U.S. Cl. ........................ 356/432; 356/444; 356/445

(58) Field of Classification Search ... 356/237.1–241.6, 356/242.1–243.8, 426–431, 600–640
See application file for complete search history.

(56) References Cited

U.S. PATENT DOCUMENTS

| | | | |
|---|---|---|---|
| 1,967,583 A * | 7/1934 | McFarlane et al. | 356/434 |
| 3,985,454 A * | 10/1976 | Fletcher et al. | 356/239.1 |
| 4,606,634 A * | 8/1986 | Bieringer | 356/239.4 |
| 4,798,956 A | 1/1989 | Hochstein | |
| 5,493,123 A * | 2/1996 | Knollenberg et al. | 250/372 |
| 5,642,198 A * | 6/1997 | Long | 356/430 |
| 6,509,967 B1 * | 1/2003 | Pingel et al. | 356/239.1 |
| 7,199,346 B2 * | 4/2007 | Stam et al. | 250/208.1 |
| 2008/0062422 A1 * | 3/2008 | Thomas et al. | 356/432 |

* cited by examiner

*Primary Examiner*—Gregory J Toatley
*Assistant Examiner*—Jarreas C Underwood
(74) *Attorney, Agent, or Firm*—Jeffrey D. Myers; Peacock Myers, P.C.; Timothy D. Stanley

(57) ABSTRACT

An apparatus and method for evaluating window transmission loss comprising taking a plurality of photographs through a filter of a window to be evaluated, determining a percentage of the window shown in each photograph that is undamaged, and computing an estimate of transmission loss for the window from the percentages determined.

22 Claims, 2 Drawing Sheets

PORTABLE EVALUATION OF WINDOW TRANSMISSION

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to devices and methods for evaluating damage to windows, including aircraft-mounted infrared windows with surface damage due to high speed impacts with sand and dust particles.

2. Description of Related Art

Infrared windows must periodically be evaluated for transmission loss resulting from surface damage due to high speed impacts with sand and dust particles in flight. Currently, these windows have to be removed for evaluation back at the window supplier. Typically this requires removal of the window from the aircraft in which the window is mounted, sending it back to a supplier, and measuring it with an infrared instrument costing on the order of $250,000. Thus, a need exists for making such evaluations in the field and/or in situ with inexpensive equipment.

It has been suggested that a portable scatter meter would make adequate measurement, but such an instrument was tried on the same samples used in testing of the present invention and the correlation was poor. Furthermore, this purportedly alternative device contains a laser, complicating its use in the field.

BRIEF SUMMARY OF THE INVENTION

The present invention is of an apparatus and method for evaluating window transmission loss, comprising: taking a plurality of photographs through a filter of a window to be evaluated; determining a percentage of the window shown in each photograph that is undamaged; and computing an estimate of transmission loss for the window from the percentages determined. In the preferred embodiment, taking comprises taking the plurality of photographs through a filter and a prism, most preferably a Wollistan prism. The window is illuminated, preferably using a light passed through a polarizing filter. Computing comprises averaging the determined percentages, preferably also adding a transmission loss of an original sample window to a slope multiplied by the computed average. The apparatus is preferably portable. The photographs are preferably magnified, most preferably at least about 100×.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention is of a device and method allowing surface damage area to be determined by a series of photos of the surface of a window (e.g., a silicon window), preferably taken at a magnification (most preferably 100×) using a filter, thereby allowing calculation of transmission loss. The invention uses a camera, filter, and an algorithm to determine the extent of area damaged. This damaged area prevents transmission and correlates very well with transmission loss. Analyses of test samples from sand and dust testing have shown that results from the invention correlate well with actual transmission loss in the 3 to 5 mid-wavelength range. With 13 sample reference points, measurement of transmission loss via the invention would take approximately 13 minutes or less.

Figure 1:
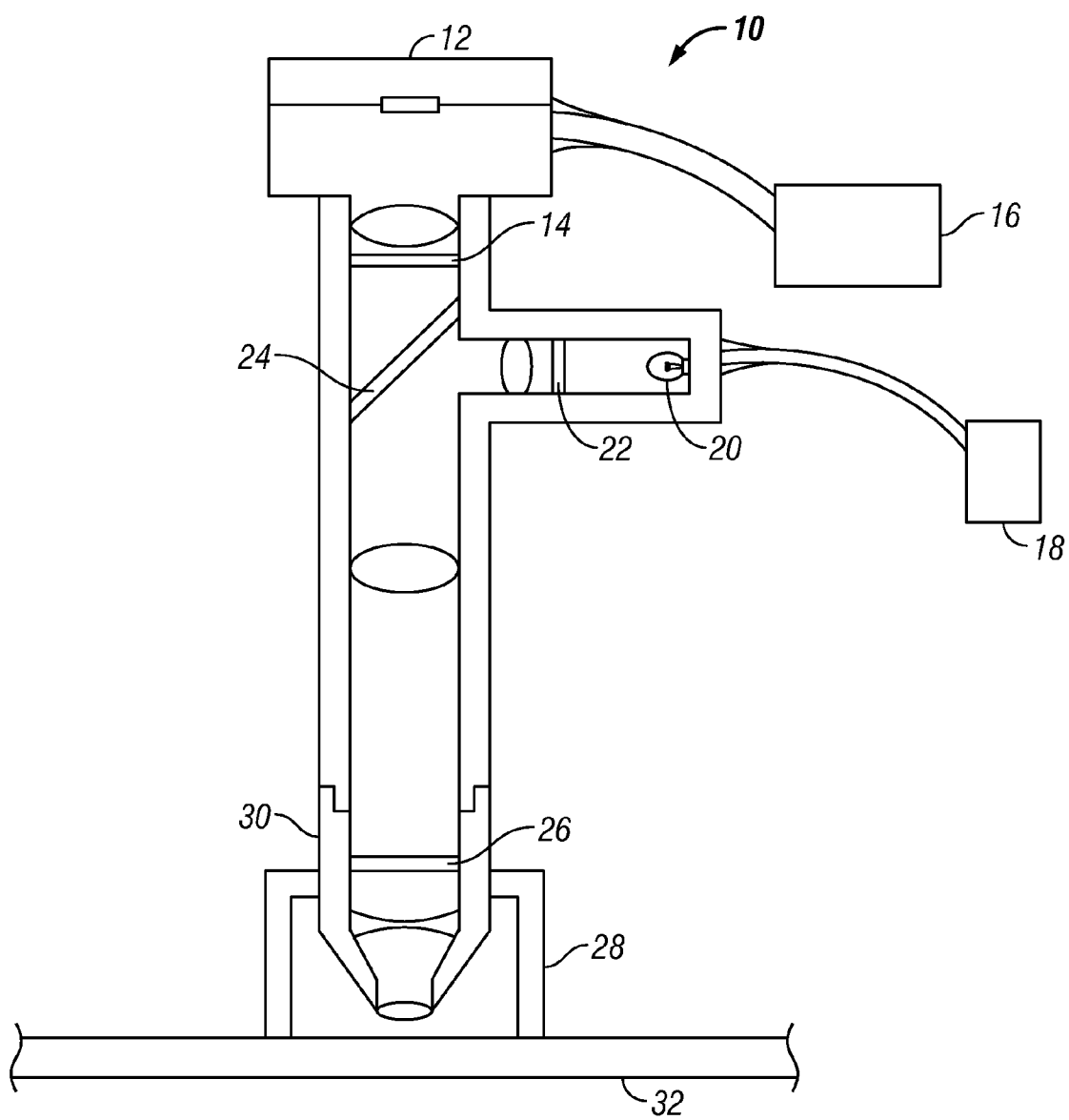
FIG. 1 is a schematic diagram of a device according to the invention.

FIG. 1 is a schematic diagram of the device 10 according to the invention for analyzing window under test 32, the device comprising camera 12, analyzer filter 14, processing unit 16, power supply 18, light source 20, polarizing filter 22, reflector 24, prism 26, stand-off 28, and interchangeable nosepiece 30. Camera images are passed through the analyzing filter and the results are analyzed by processing unit 16. Camera 12 is preferably a digital camera (e.g., a camera chip with lenses) providing for magnification, preferably of at least 100×. Filters 14 and 22 are preferably rotatable. Processing unit 16 can be any appropriate computing hardware, software, firmware, or a combination thereof, including central processing units, field-programmable gate arrays, and like units.

The light source is preferably a lamp (e.g., a halogen lamp), light-emitting diode (LED), or plurality of LEDs. The prism is preferably a Wollistan prism. The interchangeable nosepiece provides for varying amounts of magnification. Preferably, the overall illumination technique used is known as differential interference contrast.

One or more (preferably a plurality) micro photographs are taken of a window to be evaluated (e.g., 13 micro photographs) which are compared to an original sample. Each micro photograph is evaluated to determine percentage of undamaged area of the window (based upon intensity levels of the matching individual pixels within the corresponding digital images). An average over all the micro photographs is determined. This percentage is compared to that of the original sample (usually zero). The transmission loss is calculated by adding the transmission loss of the original sample to a slope multiplied by the average percentage loss calculated for the window.

Figure 2:
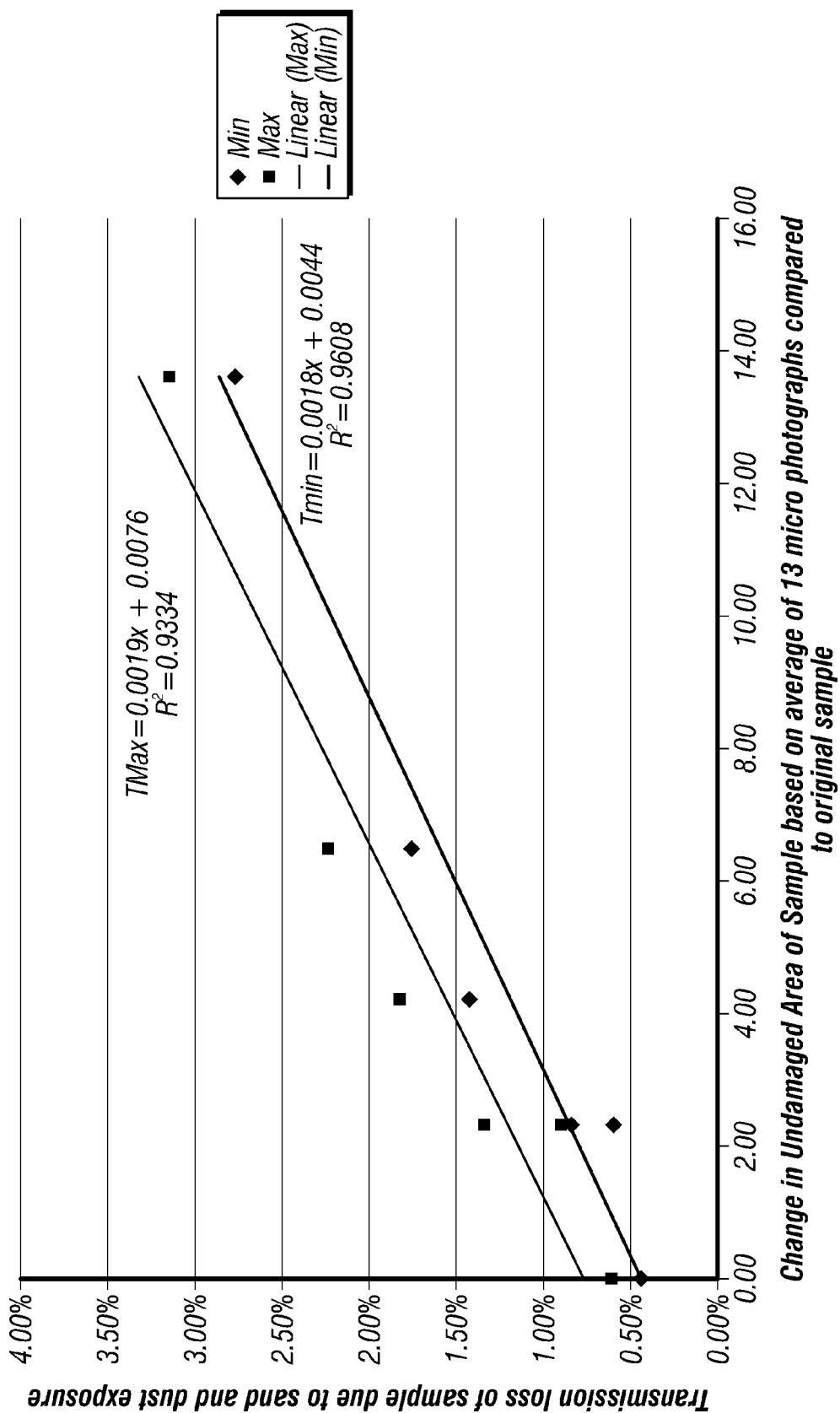
FIG. 2 is a graph illustrating the basis for the method of the invention.

FIG. 2 shows test results and a concomitant calculation method for a test sample. With $R^2$ of 93%, the maximum transmission loss is $0.0019x+0.0044$, where x is the percentage change in the undamaged area of sample as against the original specimen.

A hand-held version of the present invention preferably uses a camera chip and lenses to provide images which are evaluated by an on board processor. The resulting device is quite similar to a camera phone, and may even be included as part of a camera phone.

Note that in the specification and claims, "about" or "approximately" means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for evaluating aircraft window transmission loss, the method comprising the steps of:
   taking a plurality of photographs through a filter of an aircraft window to be evaluated;
   determining a percentage of the window shown in each photograph that is undamaged; and
   computing an estimate of transmission loss for the window from the percentages determined.

2. The method of claim 1 wherein the taking step comprises taking the plurality of photographs through a filter and a prism.

3. The method of claim 2 wherein the taking step comprises taking the plurality of photographs through a filter and a Wollistan prism.

4. The method of claim 1 additionally comprising the step of illuminating the window.

5. The method of claim 4 wherein the illuminating step comprises illuminating the window using a light passed through a polarizing filter.

6. The method of claim 1 wherein the computing step comprises averaging the determined percentages.

7. The method of claim 6 wherein the computing step comprises adding a transmission loss of an original sample window to a slope multiplied by the computed average.

8. The method of claim 1 wherein the method is conducted using a portable device.

9. The method of claim 1 wherein the taking step comprises taking magnified photographs.

10. The method of claim 9 wherein the taking step comprises taking magnified photographs at a magnification of at least about 100×.

11. The method of claim 1 wherein the determining step comprises comparing intensity values of individual pixels against expected values for an undamaged window.

12. An apparatus for evaluating aircraft window transmission loss, said apparatus comprising:
    a filter through which a camera takes a plurality of photographs of an aircraft window to be evaluated; and
    a processing unit determining a percentage of the window shown in each photograph that is undamaged and computing an estimate of transmission loss for the window from the percentages determined.

13. The apparatus of claim 12 additionally comprising a prism through which the plurality of photographs is taken.

14. The apparatus of claim 13 wherein said prism is a Wollistan prism.

15. The apparatus of claim 12 additionally comprising a light source illuminating the window.

16. The apparatus of claim 15 additionally comprising a polarizing filter through which light from said light source passes before illuminating the window.

17. The apparatus of claim 12 wherein said processing unit averages the determined percentages.

18. The apparatus of claim 17 wherein said processing unit adds a transmission loss of an original sample window to a slope multiplied by the computed average.

19. The apparatus of claim 12 wherein said apparatus is portable.

20. The apparatus of claim 12 additionally comprising a magnifying device through which the photographs are taken.

21. The apparatus of claim 20 wherein said magnifying device magnifies at least about 100×.

22. The apparatus of claim 12 wherein said processing unit compares intensity values of individual pixels against expected values for an undamaged window.

* * * * *